United States Patent [19]
Ogawa et al.

[11] Patent Number: 4,783,397
[45] Date of Patent: Nov. 8, 1988

[54] SILVER HALIDE COLOR PHOTOGRAPHIC MATERIAL CONTAINING A COUPLER FOR FORMING A YELLOW DYE, AND A PROCESS FOR PRODUCING YELLOW IMAGES USING THE SAME

[75] Inventors: Akira Ogawa; Toshiyuki Watanabe, both of Kanagawa, Japan

[73] Assignee: Fuji Photo Film Co., Ltd., Kanagawa, Japan

[21] Appl. No.: 947,302

[22] Filed: Dec. 29, 1986

[30] Foreign Application Priority Data

Dec. 27, 1985 [JP] Japan .................. 60-295893

[51] Int. Cl.$^4$ ............................. G03C 7/36
[52] U.S. Cl. ............................. 430/389; 430/557
[58] Field of Search .................. 430/389, 556, 557

[56] References Cited

U.S. PATENT DOCUMENTS 3,933,501  1/1976  Cameron et al. .............. 430/505
4,401,752  8/1983  Lau ............................... 430/389
4,511,649  4/1985  Ogawa et al. .................. 430/389

FOREIGN PATENT DOCUMENTS 21738  2/1983  Japan .
42046  3/1983  Japan .

Primary Examiner—Paul R. Michl
Assistant Examiner—Mark R. Buscher
Attorney, Agent, or Firm—Sughrue, Mion, Zinn, Macpeak, and Seas

[57] ABSTRACT

A silver halide color photographic material comprising a support having coated thereon at least one light-sensitive silver halide emulsion layer containing a yellow coupler represented by formula (I):

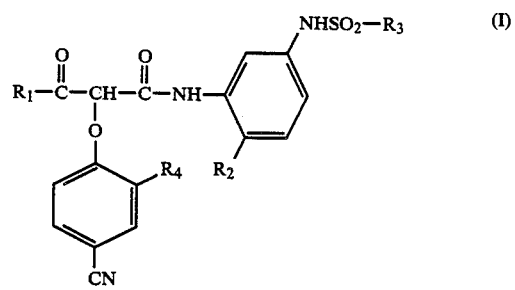

wherein $R_1$ represents a substituted or unsubstituted tertiary alkyl or aryl group; $R_2$ represents a chlorine atom or an alkoxy group; $R_3$ represents a substituted or unsubstituted alkyl or aryl group; $R_4$ represents a chlorine atom when $R_1$ represents a tertiary alkyl group or represents a hydrogen atom or a chlorine atom when $R_1$ represents an aryl group, and a process for forming yellow images using the same. The material can be processed by a developer solution that contains no benzyl alcohol.

7 Claims, No Drawings

SILVER HALIDE COLOR PHOTOGRAPHIC MATERIAL CONTAINING A COUPLER FOR FORMING A YELLOW DYE, AND A PROCESS FOR PRODUCING YELLOW IMAGES USING THE SAME

FIELD OF THE INVENTION

The present invention relates to a silver halide color photographic material containing a coupler for forming a color photographic image and, more particularly, to a silver halide color photographic material containing a novel coupler for forming a yellow dye, and a method for producing yellow images using the same.

By using the silver halide color photographic material of the present invention, a yellow dye image is obtained in the presence of the yellow coupler, which has excellent solubility, dispersion stability and spectral absorption characteristics, particularly, high color-forming rate, a high coloring density, excellent storage stability, and the coupling reactivity stable to pH change in the color developing solution which does not contain benzyl alcohol.

BACKGROUND OF THE INVENTION

As is well known, a subtractive color process comprises reducing exposed silver halide grains by an aromatic primary amine type color developing agent to prepare an oxidation product of the color developing agent and coupling the oxidation product thereof with couplers which form yellow, cyan and magenta dyes in the silver halide emulsion to form color images.

In such a process, as a yellow coupler for forming a yellow dye a compound having an active methylene group is used, as a magenta coupler for forming a magenta dye a compound of the pyrazolone type, pyrazolone benzimidazole type, indazolone type and the like is used, and as a cyan coupler for forming a cyan dye a compound of the phenol type and a compound of the naphthol type are used.

Each coupler is dissolved in a water-insoluble organic solvent having a high boiling point, with an auxiliary solvent, if necessary, and is added to a silver halide emulsion, or each coupler is added into the emulsion as an aqueous alkaline solution. Generally, the former case is preferable over the latter case in terms of light resistance, moisture resistance, heat resistance, granularity and color sharpness.

Each coupler is substantially required to have properties such that the coupler not only forms a dye but also has high solubility for an organic solvent having a high boiling point or for an alkaline solution, high dispersibility and stability in a silver halide photographic emulsion. In addition, the thus formed dye should be fast to light, heat and moisture, its spectral absorption characteristic should be excellent, its transparency should be excellent, its images should be clear and sharp and, importantly, its coloring density and color forming rate should be high.

In order to reduce the cost for treating waste solutions, it is necessary to remove benzyl alcohol which is added at color development. Generally, when a color developing solution contianing no benzyl alcohol is used, it is very common that the coloring properties of a coupler added to a silver halide photographic emulsion, such as the color forming rate and the maximum coloring density, are disadvantageously effected. Accordingly, it is desirable that the coloring properties of a yellow coupler do not depend on benzyl alcohol and that the storage of images is improved. Further, it is required to strictly control the pH condition at color development because a conventional yellow coupler has generally a high dependence on pH. In fact, it is very common that the optimum pH of color development changes with each color developing agent, coupler or a combination of couplers. Therefore, a yellow coupler having less pH dependence is required.

It is known that skeleton structures of a yellow coupler include pivaloylacetanilide type, benzoylacetanilide type, malondiester type, malondiamide type, dibenzoylmethane type, benzothiazolylacetamide type, malonester monoamide type, benzothiazolyl acetate type, benzoxazolylacetamide type, benzoxazolyl acetate type, benzimidazolylacetamide type or benzimidazolyl acetate type couplers. Of these couplers, benzoylacetanilide type and pivaloylacetanilide type couplers are preferred.

Specific examples of the above-described yellow couplers are disclosed in U.S. Pat. Nos. 2,875,057, 3,265,506, 3,408,194, 3,551,155, 3,582,322, 3,725,072, 4,356,258, 3,891,445, German Pat. No. 1,547,868, German Patent Application (OLS) Nos. 2,219,917, 2,261,361, 2,414,006, British Pat. No. 1,425,020, Japanese Patent Publication No. 10783/76, Japanese Patent Application (OPI) Nos. 26133/72, 73147/73, 102636/76, 6341/75, 123342/75, 130442/75, 21827/76, 87650/75, 82424/77 and 115219/77 (the term "OPI" as used herein refers to a "published unexamined Japanese patent application").

In order to develop yellow couplers of the α-benzoylacetanilide type and the α-pivaloylacetanilide type which meet the above-described requirements, it has been proposed to devise a structure of sulfonamide group to be introduced into the anilide nuclei. However, until now a yellow coupler having all of the above-described desirable properties has not been developed.

Specific examples of yellow couplers of α-pivalylacetanilide having an alkyl sulfonamide bond, an alkaryl sulfonamide bond, an aralkyl sulfonamide bond, a phenyl sulfonamide bond and an alkoxyphenyl sulfonamide bond at the 5-position, and whose hydrogen atom at an active side is substituted by a phenoxy group having a carboxy group, a nitro group, a 4-benzyloxyphenylsulfonyl group, a 2-alkoxyphenylsulfamoyl group, an alkylsulfamoyl group, a 4-hydroxyphenylsulfonyl group, an alkylphenylsulfonyl group, a phenylsulfonyl group, an alkylsulfonyl group or a cyano group at the 4-position are disclosed in U.S. Pat. Nos. 3,933,501 and 3,894,875.

These yellow couplers do not exhibit satisfactory coupling reactivity in the color developing solution in which benzyl alcohol is removed. Further, a comparatively high active coupler having a 4-hydroxyphenylsulfonyl phenoxy group at its active side is sensitive to changes in pH of the color developing solution. Therefore, the color density of the thus obtained color images is not uniform and the coupling activity decreases with a decreasing ratio of yellow coupler/organic solvent having a high boiling point.

In Japanese Patent Application (OPI) No. 142340/80 a yellow coupler of α-acylacetanilide containing an alkoxyalkylsulfonamide group at a non-coupling position is disclosed. It is further disclosed therein that an ether bond is introduced into a hydrophobic alkyl group part of an alkylsulfonamide group to increase the hydrophilic property, and that as a result thereof, the coupling activity of the yellow coupler is improved. However, ths thus formed dye does not have light fastness.

Yellow couplers of α-amylacetanilide having an alkylsulfonamide group which is substituted by a predetermined substituent, such as an alkylthio group, an alkyl sulfonyl group, an acyloxy group, an alkoxycarbonyl group, an amino group, a carbamoyl group, an imide group, a sulfonamide group and the like, are disclosed in Japanese Patent Application (OPI) No. 21738/83. These couplers also do not have light fastness. In addition, these couplers have a low coupling activity.

Yellow couplers of α-acylacetanilide wherein a nitrogen atom in a sulfonamide group is substituted by a substituent, such as a cyano group, a halogen atom, an alkyl group, an aryl group or a heterocyclic group and the like, are disclosed in Japanese Patent Application (OPI) No. 121126/79. However, these couplers have a low coupling reactivity and the thus formed dye is not fast to light, heat, humidity and the like.

Yellow couplers of α-acylacetanilide having a halogen atom or an alkyl group at the 2-position thereof having a halogen atom, an alkyl group or an alkoxyl group and having an alkylsulfonamide or an alkylsulfonamide substituted by a phenyl group are disclosed in Japanese Patent Application (OPI) No. 42046/83. However, these couplers have such a serious defect in that the thus formed dye has poor light fastness.

Yellow couplers of α-pivalylacetanilide having at a coupling position an aryloxy group containing a carbonyl group, a sulfonyl group or a phosphenyl group at an ortho position of the oxygen atom thereof and an alkylsulfonamide group at the 5-position thereof are disclosed in U.S. Pat. No. 4,401,752. The thus formed dye of these couplers has poor light fastness.

SUMMARY OF THE INVENTION

A first object of the present invention is to provide a novel yellow coupler having a satisfactory coupling activity when using a color developing solution having added thereto no benzyl alcohol and a method for preparing yellow dye images using the same.

A second object of the present invention is to provide a novel yellow coupler which is stable to changes in the pH of a color developing solution and has reduced unevenness of color image density.

A third object of the present invention is to provide a novel yellow coupler having excellent storage stability of the thus formed color images, that is, fastness to light, heat and moisture.

A fourth object of the present invention is to provide a novel yellow coupler having high solubility to organic solvents having a high boiling point, good dispersibility and stability to a silver halide color photographic emulsion.

A fifth object of the present invention is to provide a novel yellow coupler exhibiting satisfactory coupling activity even with the use of reduced amounts of organic solvents having a high boiling point and realizing therefore the reduction of the film thickness.

A sixth object of the present invention is to provide a photographic light-sensitive material which can be processed at a high temperature and a high speed rate by using the novel yellow coupler.

The above-described objects of the present invention have been met by developing an imagewise exposed silver halide color photographic material comprising a support having coated thereon at least one light-sensitive silver halide photographic emulsion layer containing a yellow coupler represented by formula (I) with an aromatic primary amine developing agent to form color images.

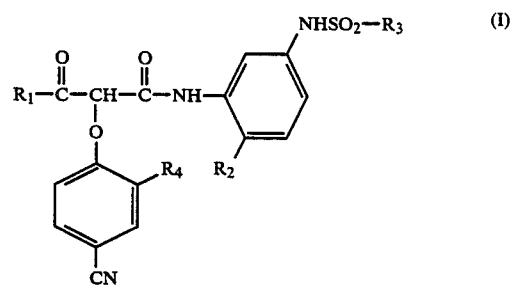

wherein $R_1$ represents a substituted or unsubstituted tertiary alkyl or aryl group, $R_2$ represents a chlorine atom or an alkoxy group, $R_3$ represents a substituted or unsubstituted alkyl or aryl group, $R_4$ represents a chlorine atom when $R_1$ represents a tertiary alkyl group, or $R_4$ represents a hydrogen atom or a chlorine atom when $R_1$ represents an aryl group.

DETAILED DESCRIPTION OF THE INVENTION

In formula (I), the tertiary alkyl groups represented by $R_1$ include unsubstituted (e.g., a t-butyl group) and substituted alkyl groups having from 4 to 8 carbon atoms. The substituents introduced into the above-described alkyl groups include halogen atoms (e.g., a fluorine atom, a chlorine atom, a bromine atom), alkoxy groups (e.g., a methoxy group, an ethoxy group), aryloxy groups (e.g., a phenoxy group, a 4-chlorophenoxy group), alkylthio groups (e.g., an n-butylthio group), arylthio groups (e.g., a phenylthio group), alkylsulfonyl groups (e.g., a methanesulfonyl group), arylsulfonyl groups (e.g., a benzenesulfonyl group), acylamino groups (e.g., an acetylamino group), amino groups (e.g., a diethylamino group) and cyano groups.

In formula (I), the aryl group represented by $R_1$ is preferably a phenyl group and may contain a substituent. The substituents of the above-described aryl group include those described above for the substituted alkyl groups and further include alkyl groups (e.g., a methyl group, an ethyl group, a t-butyl group).

In formula (I), $R_2$ represents a chlorine atom or an alkoxy group having from 1 to 4 carbon atoms (e.g., a methoxy group, an ethoxy group).

In formula (I), the alkyl group represented by $R_3$ includes an unsubstituted alkyl group having from 1 to 20 carbon atoms (e.g., an n-octyl group, a 2-ethylhexyl group, an n-dodecyl group, an n-hexadecyl group) or a substituted alkyl group. The substituents include an alkoxy group (e.g., a methoxy group), an aryloxy group (e.g., a phenoxy group, a 2-chlorophenoxy group), an aryl group (e.g., a phenyl group), an alkylthio group (e.g., a methylthio group), an arylthio group (e.g., a phenylthio group), a sulfonyl group (e.g., a methanesulfonyl group, a benzenesulfonyl group), an acyloxy group (e.g., an acetoxy group), an alkoxy- or aryloxycarbonyl group (e.g., an ethoxycarbonyl group), an amino group (e.g., a diethylamino group), an acylamino group (e.g., an acetamide group), a cyano group, and sulfonamide group (e.g., a methanesulfonamide group).

In formula (I), the aryl group represented by $R_3$ is preferably a phenyl group and may contain a substituent. The substituents of the aryl group contain those as described above for alkyl groups.

The yellow coupler represented by formula (I) has such features that one hydrogen atom at an active position is substituted by a 4-cyanophenoxy group or a 2-chloro-4-cyanophenoxy group and that the α-acylacetanilide contains a chlorine atom or an alkoxy group at the 2-position thereof and an alkylsulfonamide group or an arylsulfonamide group at the 5-position thereof. Due to the above features it is believed that the yellow coupler of the present invention has faborable characteristics.

Preferred couplers used in the present invention are represented by formula (II).

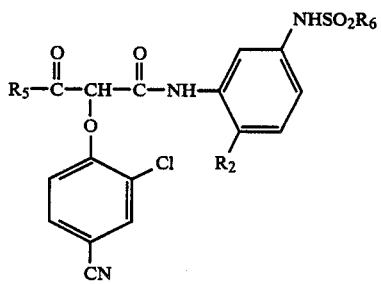
(II)

wherein $R_5$ represents a substituted or unsubstituted tertiary alkyl group having from 4 to 8 carbon atoms, $R_6$ represents an unsubstituted alkyl group or an alkyl group substituted by an alkoxy group having from 6 to 20 carbon atoms and further represents groups shown by formulae (III), (IV) and (V).

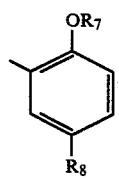
(III)

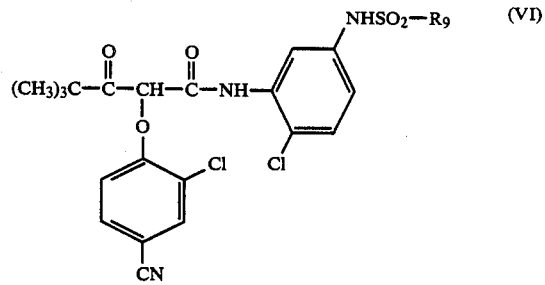

wherein $R_7$ represents an unsubstituted alkyl group or an alkyl group substituted by an alkoxy group having from 1 to 12 carbon atoms and $R_8$ represents an unsubstituted alkyl group having from 1 to 8 carbon atoms; and $R_2$ has the same definition as that in formula (I).

The most preferred couplers used in the present invention are represented by formula (VI).

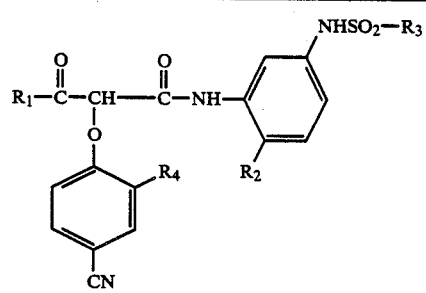
(VI)

wherein $R_9$ is an unsubstituted alkyl group having from 6 to 16 carbon atoms.

Representative examples of couplers used in the present invention are illustrated below, but the present invention is not construed as limited thereto.

(I)

| Compound No. | $R_1$ | $R_2$ | $R_3$ | $R_4$ |
|---|---|---|---|---|
| 1 | $CH_3-\underset{CH_3}{\underset{|}{\overset{CH_3}{\overset{|}{C}}}}-$ | Cl | $-C_{16}H_{33}(n)$ | Cl |

-continued

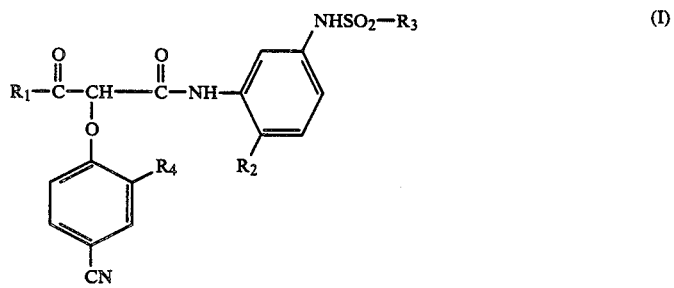

| Compound No. | R₁ | R₂ | R₃ | R₄ |
|---|---|---|---|---|
| 2 | $CH_3-\underset{CH_3}{\overset{CH_3}{C}}-$ | Cl | $-C_{12}H_{25}(n)$ | Cl |
| 3 | $CH_3-\underset{CH_3}{\overset{CH_3}{C}}-$ | Cl | 2-methyl-4-methyl-phenyl with $OC_8H_{17}(n)$ | Cl |
| 4 | $CH_3-\underset{CH_3}{\overset{CH_3}{C}}-$ | Cl | 2-methyl-4-$C_8H_{17}(t)$-phenyl with $OC_8H_{17}(n)$ | Cl |
| 5 | $CH_3-\underset{CH_3}{\overset{CH_3}{C}}-$ | Cl | 2-methyl-4-methyl-phenyl with $OCH_2CH(C_2H_5)(CH_2)_3CH_3$ | Cl |
| 6 | $CH_3-\underset{CH_3}{\overset{CH_3}{C}}-$ | Cl | 2-methyl-5-$OC_6H_{13}(n)$-phenyl with $OC_6H_{13}(n)$ | Cl |
| 7 | $CH_3-\underset{CH_3}{\overset{CH_3}{C}}-$ | Cl | 2-methyl-4,5-dimethyl-phenyl with $OC_8H_{17}(n)$ | Cl |
| 8 | $CH_3-\underset{CH_3}{\overset{CH_3}{C}}-$ | Cl | 2-methyl-4-$C_8H_{17}(t)$-phenyl with $OC_2H_5$ | Cl |

-continued

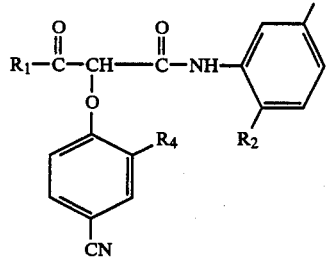
(I)

| Compound No. | R₁ | R₂ | R₃ | R₄ |
|---|---|---|---|---|
| 9 | $CH_3-\underset{\underset{CH_3}{|}}{\overset{\overset{CH_3}{|}}{C}}-$ | Cl | 2-methyl-4,... phenyl with $OC_8H_{17}(n)$ at 2 and 5 positions | Cl |
| 10 | $CH_3-C(CH_3)_2-CH_3$ (t-Bu) | —OCH₃ | phenyl with $O(CH_2)_2OC_2H_5$ and $C_8H_{17}(t)$ | Cl |
| 11 | t-Bu | —OCH₃ | phenyl with $O-(CH_2)_2OC_2H_5$ and two CH₃ | Cl |
| 12 | t-Bu | —OCH₃ | phenyl with $O(CH_2)_2OC_2H_5$ and $C_5H_{11}(t)$ | Cl |
| 13 | t-Bu | —OCH₃ | phenyl with $O(CH_2)_2OC_4H_9(n)$ at two positions | Cl |
| 14 | t-Bu | —OCH₃ | phenyl with $OCH_2CH(C_2H_5)(CH_2)_3CH_3$ at two positions | Cl |
| 15 | t-Bu | —OCH₃ | phenyl with $OC_4H_9(n)$ at two positions | Cl |
| 16 | $CH_3O-\text{C}_6H_4-$ | Cl | —C₁₆H₃₃(n) | H |

-continued

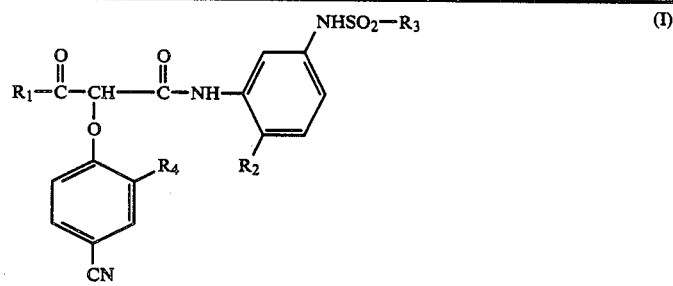

| Compound No. | $R_1$ | $R_2$ | $R_3$ | $R_4$ |
|---|---|---|---|---|
| 17 | CH$_3$O—C$_6$H$_4$— | Cl | —C$_{16}$H$_{33}$(n) | Cl |
| 18 | CH$_3$O—C$_6$H$_4$— | Cl | 2-methyl-4-(OC$_6$H$_{13}$(n))-phenyl | H |
| 19 | CH$_3$—C$_6$H$_4$— | Cl | 2-(OC$_6$H$_{13}$(n))-4-(OC$_6$H$_{13}$(n))-phenyl | Cl |
| 20 | 4-CH$_3$O-2-OCH$_3$-phenyl | Cl | 2-OCH$_3$-4-C$_8$H$_{17}$(t)-phenyl | H |
| 21 | 2-OCH$_3$-phenyl | —OCH$_3$ | 2-OC$_8$H$_{17}$(t)-4,5-di-CH$_3$-phenyl | H |

Novel couplers in accordance with formula (I) of the present invention can be prepared by reacting α-chloro-α-acylacetanilide represented by formula (VII)

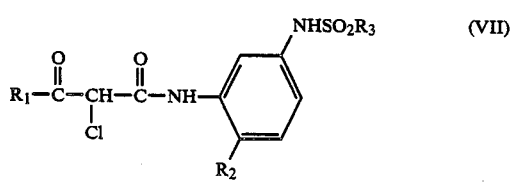

wherein $R_1$ to $R_3$ have the same definition as described above, with o-substituted p-cyanophenol represented by formula (VIII)

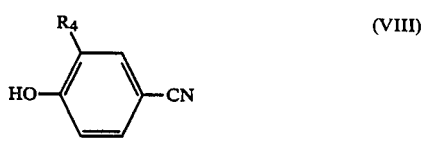

wherein $R_4$ has the same definition as described above, in the presence of base if necessary. A reaction temperature ranges from 20° to 90° C., preferably 30° to 60° C. The molar ratio of α-chloro-α-acylacetanilide and p-cyanophenol is generally 1 to 5, preferably 1.5 to 3.

Couplers represented by formula (VII) and couplers of the present invention represented by formula (I) can easily be synthesized in accordance with the methods disclosed in U.S. Pat. Nos. 3,265,506, 3,408,194, Japanese Patent Application (OPI) Nos. 99433/79 and 115219/77.

p-Cyanophenol represented by formula (VIII) is a known compound and can be snythesized by chlorinating p-cyanophenol with sulfuryl chloride when $R_4$ is a chlorine atom, as disclosed in Beilstein, 10, 176.

Two or more couplers of the present invention can be added to one layer and one type of coupler can be added to two or more layers, respectively. The couplers of the present invention can be used in combination with known pivaloylacetanilide type and benzoylacetanilide type couplers, such as nitrogen atom released type yellow couplers as disclosed in Japanese Patent Publication No. 10739/83, U.S. Pat. Nos. 4,401,752, 4,326,024, Research Disclosure, No. 18053 (April, 1979), British Pat. No. 1,425,020, German Patent Application (OLS) Nos. 2,219,917, 2,261,361, 2,329,587 and 2,433,812, or oxygen atom released type yellow couplers as disclosed in U.S. Pat. Nos. 3,408,194, 3,447,928, 3,933,501 and 4,022,620.

When the couplers of the present invention are used in combination with known couplers, it is preferred that couplers of the present invention are used in a high sensitive blue-sensitive emulsion layer and nitrogen atom released type yellow couplers are added to a low sensitive blue-sensitive emulsion layer.

The couplers of the present invention are generally added in an amount of $2 \times 10^{-3}$ to $5 \times 10^{-1}$ mol, preferably $1 \times 10^{-2}$ to $5 \times 10^{-1}$ mol, per mol of silver in an emulsion.

When the couplers of the present invention are used in combination with the above-described couplers, it is preferred that the total additive amounts of couplers which form the same color fall within the above ranges.

The silver halide color photographic materials containing yellow couplers of the present invention have different silver halide compositions, additives and supports in accordance with their intended purpose, can be prepared in accordance with a conventional method (as described in Research Disclosure, No. 18716 (November, 1979) and ibid., No. 17643 (December, 1978) and can be used for both color negative films and color reversal films.

The light-sensitive materials in accordance with the present invention can be developed by any conventional methods (as described in the above-mentioned references).

The present invention is further illustrated by the following non-limiting examples. Unless otherwise indicated, all percents, parts and ratios are by weight.

Typical examples of preparing the couplers of the present invention are shown below.

SYNTHESIS EXAMPLE 1

Coupler 1

To a mixture of 21.5 g of 2-chloro-4-cyanophenol and 200 ml of acetonitrile was added 21.5 ml of triethylamine. To the solution was dropwise added a solution of 41.4 g of α-chloro-α-pivaloyl-2-chloro-5-(n-hexadecanesulfonamido)acetanilide dissolved in 50 ml of acetonitrile with stirring at 30° to 40° C.

After the solution was added dropwise, the reaction was carried out for 4 hours at 40° C., and the reaction mixture was introduced into 400 ml of water having dissolved therein 4 g of sodium hydroxide. The solution was then extracted with 500 ml of ethyl acetate. The oil layer was washed with water, made acidic with dilute hydrochloric acid and again washed with water. The oil layer was dried in the presence of magnesium sulfate and concentrated under reduced pressure to obtain 50 g of the residue.

The residue was crystallized from a mixed solvent of 5 ml of isopropanol and 500 ml of n-hexane to obtain 36 g of white crystals. These crystals were recrystallized from a mixed solvent of 40 ml of isopropanol and 400 ml of n-hexane to obtain 32 g of Coupler 1. Melting Point: 103° to 104° C.

SYNTHESIS EXAMPLE 2

Coupler 3

To a mixture of 21.5 g of 2-chloro-4-cyanophenol and 200 ml of acetonitrile was added 21.5 ml of triethylamine. To the resulting solution was dropwise added a solution of 400 ml of acetonitrile having dissolved therein 41 g of α-chloro-α-pivaloyl-2-chloro5-[(2-n-octyloxy-5-methyl)benzenesulfonamido]acetanilide with stirring at 30° to 40° C. After the solution was added dropwise, the reaction was carried out for 3 hours at 40° to 45° C. and was cooled to 5° C. Then, the separated crystals were collected by filtration. Yield: 38.2 g, Melting Point: 149° to 150° C.

These crystals were recrystallized from 400 ml of acetonitrile to obtain 32 g of Coupler 3. Melting Point: 152 to 153° C.

SYNTHESIS EXAMPLE 3

Coupler 6

To a mixture of 19.4 g of 2-chloro-4-cyanophenol and 200 ml of acetonitrile was added 19.4 ml of triethylamine. To the resulting solution was dropwise added a solution of 50 ml of acetonitrile having dissolved therein 40.6 g of α-chloro-α-pivaloyl-2-chloro-5-[(2,4-di-n-hexyloxy)benzenesulfonamido]acetanilide with stirring at 30° to 40° C. After the solution had been added dropwise, the reaction was carried out at 35° to 40° C. for 4 hours. Then, the solution was introduced into 400 ml of an aqueous solution containing 3.5 g of sodium hydroxide and the reaction mixture was extracted with 500 ml of ethyl acetate. The oil layer was washed with water and made acidic with dilute hydrochloric acid and washed again with water.

The oil layer was dried in the presence of magnesium sulfate and concentrated under reduced pressure to obtain 45 g of the residue. The residue was crystallized from a mixed solvent of 60 ml of ethyl acetate and 400 ml of n-hexane to obtain 40 g of white crystals. Melting Point: 114° to 118° C. These crystals were recrystallized from 50 ml of ethyl acetate and 100 ml of n-hexane to obtain 30.0 g of Coupler 6. Melting Point: 123° to 124° C.

SYNTHESIS EXAMPLE 4

Coupler 16

To a mixture of 12.6 g of p-cyanophenol and 100 ml of acetonitrile was added 14.8 ml of triethylamine. To the resulting solution was dropwise added a solution of 80 ml of acetonitrile having dissolved therein 34 g of α-chloro-α-(4-methoxybenzoyl)-2-chloro-5-(n-hexadecanesulfonamido)acetanilide at 30° to 40° C. with stirring.

After the solution was added dropwise, the solution was reacted for 3 hours at 30° to 40° C., and was added to 300 ml of an aqueous solution containing 2.1 g of sodium hydroxide. Then, the reaction mixture was extracted with 400 ml of ethyl acetate. The oil layer was washed with water, made acidic with dilute hydrochloric acid and was washed with water again.

The oil layer was dried in the presence of magnesium sulfate and concentrated under reduced pressure to obtain 36 g of the residue. The residue was crystallized from ethyl acetate/n-hexane (volume ratio: 1/5, 200 ml ). The filtrated crystals were recrystallized from ethyl acetate/n-hexane (volume ratio: 1/8, 300 ml ) to obtain 25.5 g of Coupler 16. Melting Point: 119° to 120° C.

EXAMPLE 1

A photographic element having layers composed of the following compositions on a cellulose acetate film support was prepared.

First Layer:

A yellow coupler and tricresyl phosphate were mixed so that the weight mixing ratio was 3:1, 3 parts of ethyl acetate was added thereto and dissolved while being heated at 40° C. The resulting solution was dispersed and emulsified in 20 parts of a 3% aqueous gelatin solution containing 0.3% of a surface active agent (dodecylbenzene sodium sulfonate) to obtain an emulsified dispersion of the yellow coupler. The thus obtained emulsified dispersion and silver iodobromide emulsion (silver iodide: 6 mol %) were mixed to prepare a solution so that the molar ratio of silver to the coupler was 3.5:1.

Second Layer:

A 1.5% aqueous gelatin solution having mixed with 0.2% of a hardening agent (1,3-vinylsulfonyl-2-propanol) and 0.01% of a surface active agent (Triton X-200) was prepared.

Photographic elements designated Sample Nos. 101 to 113 were prepared changing yellow couplers as used in the first layer to those as shown in Table 1. The amount of coupler coated was adjusted to 1.25 mmol/m$^2$.

Further, samples wherein the weight ratio of yellow couplers and tricresyl phosphate was 10:1 were prepared (Sample Nos. 114 to 126).

Blue exposure was carried out on these samples and the following development was carried out at 38° C.

| | |
|---|---|
| 1. Color Development | 3 min 15 sec |
| 2. Bleaching | 6 min 30 sec |
| 3. Water Washing | 3 min 15 sec |
| 4. Fixation | 6 min 30 sec |
| 5. Water Washing | 3 min 15 sec |
| 6. Stabilization | 3 min 15 sec |

The composition of the processing solutions used in each step was as follows.

Color Developing Solution:

| | |
|---|---|
| Sodium Nitrotriacetate | 1.0 g |
| Sodium Sulfite | 4.0 g |
| Sodium Carbonate | 30.0 g |
| Potassium Bromide | 1.4 g |
| Hydroxylamine Sulfate | 2.4 g |
| 4-(N—Ethyl-N—β-hydroxyethylamino)-2-methylaniline Sulfate | 4.5 g |
| Water to make | 1 l |

Bleaching Solution:

| | |
|---|---|
| Ammonium Bromide | 160.0 g |
| Ammonia Water (28%) | 25.0 ml |
| Sodium Ethylenediaminetetraacetate Iron Salt | 130 g |
| Glacial Acetic Acid | 14 ml |
| Water to make | 1 l |

Fixing Solution:

| | |
|---|---|
| Sodium Tetrapolyphosphate | 2.0 g |
| Sodium Sulfite | 4.0 g |
| Ammonium Thiosulfate (70%) | 175.0 ml |
| Sodium Bisulfite | 4.6 g |
| Water to make | 1 l |

Stabilizing Solution:

| | |
|---|---|
| Formaldehyde | 8.0 ml |
| Water to make | 1 l |

Couplers used for comparison:

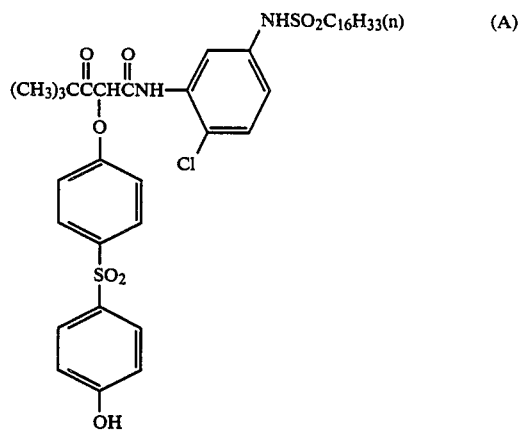

(Disclosed in U.S. Pat. No. 3,933,501)

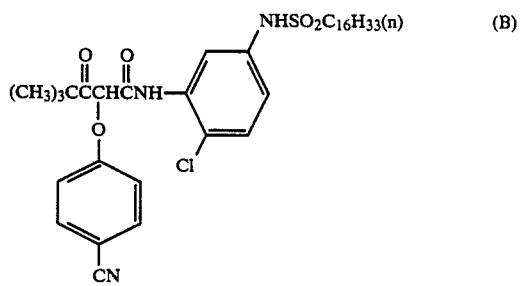

(Disclosed in U.S. Pat. No. 3,933,501)

-continued

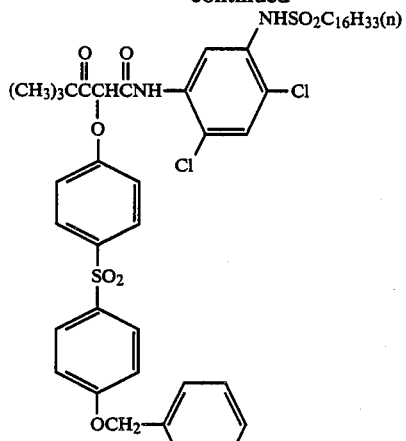

(Disclosed in Japanese Patent Application (OPI) No. 42046/83)

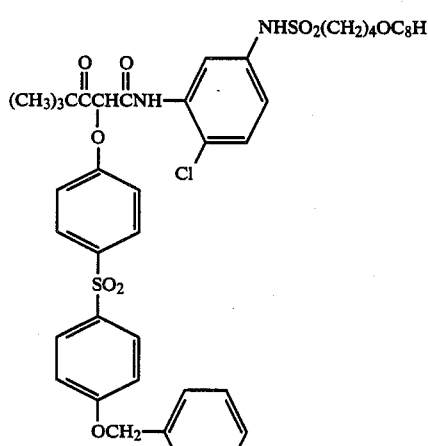

(Disclosed in Japanese Patent Application (OPI) No. 142340/80)

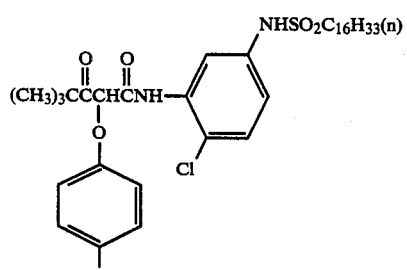

(Disclosed in U.S. Pat. No. 3,894,875)

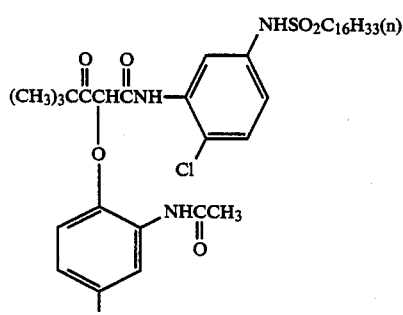

(Disclosed in U.S. Pat. No. 4,401,752)

TABLE 1

| Sample No. | Coupler | Tricresyl Phosphate/ Coupler (wt/wt) | Fog | Gamma | Relative Sensitivity* |
|---|---|---|---|---|---|
| 101 | Coupler 1 | 0.33 | 0.03 | 1.50 | 110 |
| 114 | " | 0.10 | 0.03 | 1.49 | 105 |
| 102 | Coupler 4 | 0.33 | 0.03 | 1.43 | 108 |
| 115 | " | 0.10 | 0.03 | 1.43 | 108 |
| 103 | Coupler 5 | 0.33 | 0.03 | 1.41 | 107 |
| 116 | " | 0.10 | 0.03 | 1.41 | 107 |
| 104 | Coupler 6 | 0.33 | 0.04 | 1.46 | 108 |
| 117 | " | 0.10 | 0.02 | 1.45 | 108 |
| 105 | Coupler 8 | 0.33 | 0.04 | 1.48 | 107 |
| 118 | " | 0.10 | 0.03 | 1.45 | 105 |
| 106 | Coupler 9 | 0.33 | 0.03 | 1.40 | 105 |
| 119 | " | 0.10 | 0.04 | 1.38 | 104 |
| 107 | Coupler 14 | 0.33 | 0.03 | 1.41 | 107 |
| 120 | " | 0.10 | 0.02 | 1.37 | 106 |
| 108 | Comparative Coupler (A) | 0.33 | 0.03 | 1.43 | 100 |
| 121 | Comparative Coupler (A) | 0.10 | 0.04 | 1.10 | 75 |
| 109 | Comparative Coupler (B) | 0.33 | 0.04 | 1.31 | 90 |
| 122 | Comparative Coupler (B) | 0.10 | 0.03 | 1.26 | 80 |
| 110 | Comparative Coupler (C) | 0.33 | 0.03 | 1.33 | 94 |
| 123 | Comparative Coupler (C) | 0.10 | 0.04 | 1.28 | 81 |
| 111 | Comparative Coupler (D) | 0.33 | 0.04 | 1.30 | 90 |
| 124 | Comparative Coupler (D) | 0.10 | 0.05 | 1.18 | 75 |
| 112 | Comparative Coupler (E) | 0.33 | 0.04 | 1.28 | 85 |
| 125 | Comparative Coupler (E) | 0.10 | 0.05 | 1.15 | 70 |
| 113 | Comparative Coupler (F) | 0.33 | 0.05 | 1.21 | 80 |
| 126 | Comparative Coupler (F) | 0.10 | 0.05 | 1.05 | 70 |

*Relative sensitivity is a reciprocal of the exposure amount necessary to give a density of fog + 0.2 and is shown by a relative value when the sensitivity of Sample No. 108 is 100.

It is clear from Table 1 that the present invention exhibits a high gamma, a high sensitivity and a high color forming property (high color density) without increasing fog.

Comparative Coupler (A) exhibited a comparatively high color forming property (high color density) when the ratio of tricresyl phosphate/coupler has high (Sample No. 108), and exhibited great low contrast and reduced sensitivity when the amount of tricresyl phosphate was reduced. On the other hand, it is apparent that the color forming property of the yellow 2-equivalent coupler of the present invention does not depend upon the amount of tricresyl phosphate employed.

EXAMPLE 2

A photographic element having layers composed of the following compositions on a paper support on both surfaces of which were laminated with polyethylene was prepared.

First Layer:

A yellow coupler and di-n-butylphthalate were mixed so that the weight mixing ratio was 8:1, 3 parts of ethyl acetate was added thereto and dissolved while being heated at 40° C. The resulting solution was dispersed and emulsified in a 3% aqueous gelatin solution containing 0.3% of a surface active agent (dodecylbenzene sodium sulfonate) to obtain an emulsified dispersion of yellow coupler. A solution was prepared wherein the thus obtained emulsified dispersion and silver chlorobromide emulsion (silver bromide: 80 mol %) were mixed so that the molar ratio of silver to coupler was 3.5:1.

Second Layer:

A 1.5% aqueous gelatin solution having mixed therewith 0.2% of a hardening agent (1,3-vinylsulfonyl-2-propanol) and 0.01% of a surface active agent (Triton X-200) was prepared.

Photographic elements designated Sample Nos. 200 to 210 were prepared changing yellow couplers used in the first layer to those as shown in Table 2. The amount of coupler coated was adjusted to 1.0 mmol/m².

TABLE 2

| Sample No. | Yellow Coupler |
| --- | --- |
| 200 (Comparison) | Comparative Coupler (A) |
| 201 (Comparison) | Comparative Coupler (B) |
| 202 (Comparison) | Comparative Coupler (D) |
| 203 (Invention) | Coupler (1) |
| 204 (Invention) | Coupler (3) |
| 205 (Invention) | Coupler (4) |
| 206 (Invention) | Coupler (6) |
| 207 (Invention) | Coupler (7) |
| 208 (Invention) | Coupler (8) |
| 209 (Invention) | Coupler (9) |
| 210 (Invention) | Coupler (11) |

On these samples, blue exposure was carried out and the following processing was carried out at 33° C.

Processing Step:

| Color Development (A) or (B) | 3 min 30 sec |
| --- | --- |
| Bleaching and Fixation | 1 min 30 sec |
| Water Washing | 3 min |
| Drying | 10 min |

The composition of the processing solutions used in each step was as follows.

Color Developing Solution (A):

| Benzyl Alcohol | 15 ml |
| --- | --- |
| Diethylene Glycol | 5 ml |
| Potassium Carbonate | 25 g |
| Sodium Chloride | 0.1 g |
| Sodium Bromide | 0.5 g |
| Anhydrous Sodium Sulfite | 2 g |
| Hydroxylamine Sulfate | 2 g |
| N—Ethyl-N—β-methanesulfonamide ethyl-3-methyl-4-aminoaniline Sulfate | 4 g |
| Water to make | 1 l |
| NaOH was added to adjust pH to 10.3 | |

Color Developing Solution (B):

Color Developing Solution (B) had the same composition as that of Color Developing Solution (A) except that benzyl alcohol was removed.

Bleaching and Fixing Solution:

| Ammonium Thiosulfate | 124.5 g |
| --- | --- |
| Sodium Metabisulfite | 13.3 g |
| Anhydrous Sodium Sulfite | 2.7 g |
| (Ethylenediaminetetraacetato)-iron (III) Ammonium Salt | 65 g |
| Water to make | 1 l |
| pH was adjusted to 6.8 | |

The color density of the thus developed samples was measured and the results of fog, gamma and $D_{max}$ of each sample are shown in Table 3.

A test of the storage stability of the color images was conducted in the following manner (a) and (b).

(a) Light Fastness

| | | Lux | Period of Irradiation (hours) |
| --- | --- | --- | --- |
| A: | Xenon fade meter | $3.5 \times 10^4$ | 100 |
| B: | Luminescent lamp color fade testing machine | $1.6 \times 10^4$ | 300 |

(b) Light Fastness in Darkness

| C: 80° C. | Adding no moisture | 40 days |
| --- | --- | --- |
| D: 70° C. | 80% RH | 40 days |

The storage stability of the color images is shown in terms of percent of the density (D) after testing to the initial density ($D_o$) = 1.0. The results are shown in Table 4.

Further, in order to check the influence of pH in Color Developing Solution (A) on the color forming property, the development was conducted changing the pH in a color developing bath with NaOH or phosphoric acid. The relative sensitivity of the thus developed sample strips is shown in Table 5.

TABLE 3

| | Color Developing Solution (A) | | | Color Developing Solution (B) | | |
| --- | --- | --- | --- | --- | --- | --- |
| Sample No. | Fog | Gamma | $D_{max}$ | Fog | Gamma | $D_{max}$ |
| 200 (Comparison) | 0.08 | 2.30 | 2.20 | 0.08 | 2.08 | 2.10 |
| 201 (Comparison) | 0.09 | 2.08 | 1.98 | 0.09 | 1.95 | 1.80 |
| 202 (Comparison) | 0.08 | 2.04 | 1.99 | 0.08 | 1.80 | 1.78 |
| 203 (Invention) | 0.07 | 2.31 | 2.24 | 0.07 | 2.18 | 2.18 |
| 204 (Invention) | 0.08 | 2.40 | 2.32 | 0.08 | 2.32 | 2.30 |
| 205 (Invention) | 0.09 | 2.39 | 2.40 | 0.07 | 2.34 | 2.32 |
| 206 (Invention) | 0.08 | 2.34 | 2.31 | 0.07 | 2.30 | 2.29 |
| 207 (Invention) | 0.07 | 2.38 | 2.33 | 0.08 | 2.35 | 2.30 |
| 208 (Invention) | 0.07 | 2.40 | 2.32 | 0.08 | 2.35 | 2.29 |
| 209 (Invention) | 0.08 | 2.38 | 2.38 | 0.08 | 2.35 | 2.31 |
| 210 (Invention) | 0.08 | 2.40 | 2.31 | 0.08 | 2.36 | 2.31 |

TABLE 4

| | Light Fastness | | Light Fastness in Dark | |
| --- | --- | --- | --- | --- |
| Sample No. | A | B | C | D |
| 200 | 73 | 76 | 75 | 73 |
| 201 | 63 | 79 | 72 | 71 |
| 202 | 61 | 59 | 70 | 71 |
| 203 | 74 | 79 | 79 | 79 |
| 204 | 86 | 85 | 80 | 82 |
| 205 | 85 | 80 | 82 | 81 |
| 206 | 89 | 85 | 83 | 84 |
| 207 | 89 | 87 | 80 | 80 |
| 208 | 90 | 88 | 80 | 81 |
| 209 | 89 | 89 | 81 | 80 |
| 210 | 83 | 83 | 80 | 83 |

TABLE 5

| | pH Value of Color Developing Solution | | |
| --- | --- | --- | --- |
| Sample No. | pH 10.0 | pH 10.3 | pH 10.8 |
| 200 | 90 | 100 | 140 |
| 201 | 92 | 100 | 120 |
| 202 | 95 | 100 | 125 |

TABLE 5-continued

| | pH Value of Color Developing Solution | | |
|---|---|---|---|
| Sample No. | pH 10.0 | pH 10.3 | pH 10.8 |
| 203 | 98 | 100 | 118 |
| 204 | 98 | 100 | 115 |
| 205 | 98 | 100 | 111 |
| 206 | 95 | 100 | 108 |
| 207 | 98 | 100 | 102 |
| 208 | 98 | 100 | 108 |
| 209 | 98 | 100 | 105 |
| 210 | 96 | 100 | 103 |

It is clear from Table 3 that Sample Nos. 203 to 210 exhibit better color forming property than Comparative Sample Nos. 200 to 202 and also exhibit the feature that the density and gamma hardly decrease in Color Developing Solution (B) which does not contain benzyl alcohol.

It is also apparent that, in particular, Sample No. 203 (Coupler 1) shows an excellent color forming property than Sample No. 201 (Comparative Coupler (B)) in Color Developing Solutions (A) and (B).

It is clear from Table 4 that the couplers of the present invention are excellent in light fastness and light fastness in dark and that the couplers of the present invention are remarkably improved compared with Comparative Sample Nos. 201 and 202.

It is understood from Table 5 that the finished photographic images prepared using the yellow couplers of the present invention are not influenced by pH changes in the color developing solution. The finished photographic images are remarkably improved, particularly when compared with Comparative Sample No. 200.

EXAMPLE 3

A multilayered color light-sensitive material composed of layers having the following composition respectively on an undercoated cellulose triacetate film support was prepared and designated Sample No. 301.

First Layer: Antihalation Layer

| | |
|---|---|
| Black colloidal silver | 0.25 g/m$^2$ |
| Ultraviolet Abosrbing Agent U-1 | 0.04 g/m$^2$ |
| Ultraviolet Absorbing Agent U-2 | 0.1 g/m$^2$ |
| Ultraviolet Absorbing Agent U-3 | 0.1 g/m$^2$ |
| Organic solvent having a high boiling point, 0-1 | 0.1 cc/m$^2$ |
| Gelatin | 2.5 g/m$^2$ |

Second Layer: Intermediate Layer

| | |
|---|---|
| Compound H-1 | 0.05 g/m$^2$ |
| Organic solvent having a high boiling point, 0-2 | 0.05 cc/m$^2$ |
| Gelatin | 0.6 g/m$^2$ |

Third Layer: First Red-sensitive Emulsion Layer

| | |
|---|---|
| Silver iodobromide emulsion spectrally sensitized by Sensitizing Dyes S-1 and S-2 (content of iodide: 4 mol %, average particle size: 0.3 μm) | 0.5 g/m$^2$ (silver) |
| Coupler C-1 | 0.25 g/m$^2$ |
| Organic solvent having a high boiling point, 0-2 | 0.12 cc/m$^2$ |
| Gelatin | 1.1 g/m$^2$ |

Fourth Layer: Second Red-sensitive Emulsion Layer

| | |
|---|---|
| Silver iodibromide emulsion spectrally sensitized by Sensitizing Dyes S-1 and S-2 (content of iodide: 2.5 mol %, average particle size: 0.55 μm) | 0.8 g/m$^2$ (silver) |
| Coupler C-1 | 0.73 g/m$^2$ |
| Organic solvent having a high boiling point, 0-2 | 0.37 cc/m$^2$ |
| Gelatin | 1.8 g/m$^2$ |

Fifth Layer: Intermediate Layer

| | |
|---|---|
| Compound H-1 | 0.1 g/m$^2$ |
| Organic solvent having a high boiling point, 0-2 | 0.1 cc/m$^2$ |
| Gelatin | 1.5 g/m$^2$ |

Sixth Layer: First Green-sensitive Emulsion Layer

| | |
|---|---|
| Silver iodobromide emulsion spectrally sensitized by Sensitizing Dyes S-3 and S-4 (content of iodide: 3 mol %, average particle size: 0.3 μm) | 0.7 g/m$^2$ (silver) |
| Coupler C-2 | 0.35 g/m$^2$ |
| Organic solvent having a high boiling point, 0-2 | 0.07 cc/m$^2$ |
| Gelatin | 1.5 g/m$^2$ |

Seventh Layer: Second Green-sensitive Emulsion Layer

| | |
|---|---|
| Silver iodobromide emulsion spectrally sensitized by Sensitizing Dyes S-3 and S-4 (content of iodide: 2.5 mol %, average particle size: 0.8 μm) | 0.7 g/m$^2$ |
| Coupler C-2 | 0.25 g/m$^2$ |
| Organic solvent haivng a high boiling point, 0-2 | 0.05 cc/m$^2$ |
| Gelatin | 1.3 g/m$^2$ |

Eighth Layer: Intermediate Layer

| | |
|---|---|
| Compound H-1 | 0.05 g/m$^2$ |
| Organic solvent having a high boiling point, 0-2 | 0.1 cc/m$^2$ |
| Gelatin | 0.6 g/m$^2$ |

Ninth Layer: Yellow Filter Layer

| | |
|---|---|
| Yellow colloidal silver | 0.1 g/m$^2$ |
| Compound H-1 | 0.02 g/m$^2$ |
| Compound H-2 | 0.03 g/m$^2$ |
| Organic solvent having a high boiling point, 0-2 | 0.04 cc/m$^2$ |
| Gelatin | 1.0 g/m$^2$ |

Tenth Layer: First Blue-sensitive Emulsion Layer

| | |
|---|---|
| Silver iodobromide emulsion spectrally sensitized by Sensitizing Dye S-5 (content of iodide: 2.5 mol %, average particle size: 0.7 μm) | 0.6 g/m$^2$ (silver) |
| Coupler C-3 | 0.5 g/m$^2$ |
| Organic solvent having a high boiling point, 0-2 | 0.1 cc/m$^2$ |

-continued

| Gelatin | 1.2 g/m² |

Eleventh Layer: Second Blue-sensitive Emulsion Layer

| Silver iodobromide emulsion spectrally sensitized by Sensitizing Dye S-5 (content of iodide: 2.5 mol %, average particle size: 1.2 μm) | 1.1 g/m² |
| Coupler C-1 | 1.2 g/m² |
| Organic solvent having a high boiling point, 0-2 | 0.23 cc/m² |
| Gelatin | 2.5 g/m² |

Twelfth Layer: First Protective Layer

| Ultraviolet Absorbing Agent U-1 | 0.02 g/m² |
| Ultraviolet Absorbing Agent U-2 | 0.03 g/m² |
| Ultraviolet Absorbing Agent U-3 | 0.03 g/m² |
| Ultraviolet Absorbing Agent U-4 | 0.29 g/m² |
| Organic solvent having a high boiling point, 0-1 | 0.28 cc/m² |
| Gelatin | 1.6 g/m² |

Thirteenth Layer: Second Protective Layer

| Silver iodobromide emulsion of fogged particles (content of iodide: 1 mol %, average particle size: 0.6 μm) | 0.1 g/m² |
| Polymethyl methacrylate particles (average particle size: 1.5 μm) | 0.15 g/m² |
| Gelatin | 2 g/m² |

In addition to the above composition, Gelatin Hardening Agent H-3 and a surface active agent were added in an amount as described in the second layer of Example 1.

The compounds used to prepare the samples are illustrated below.

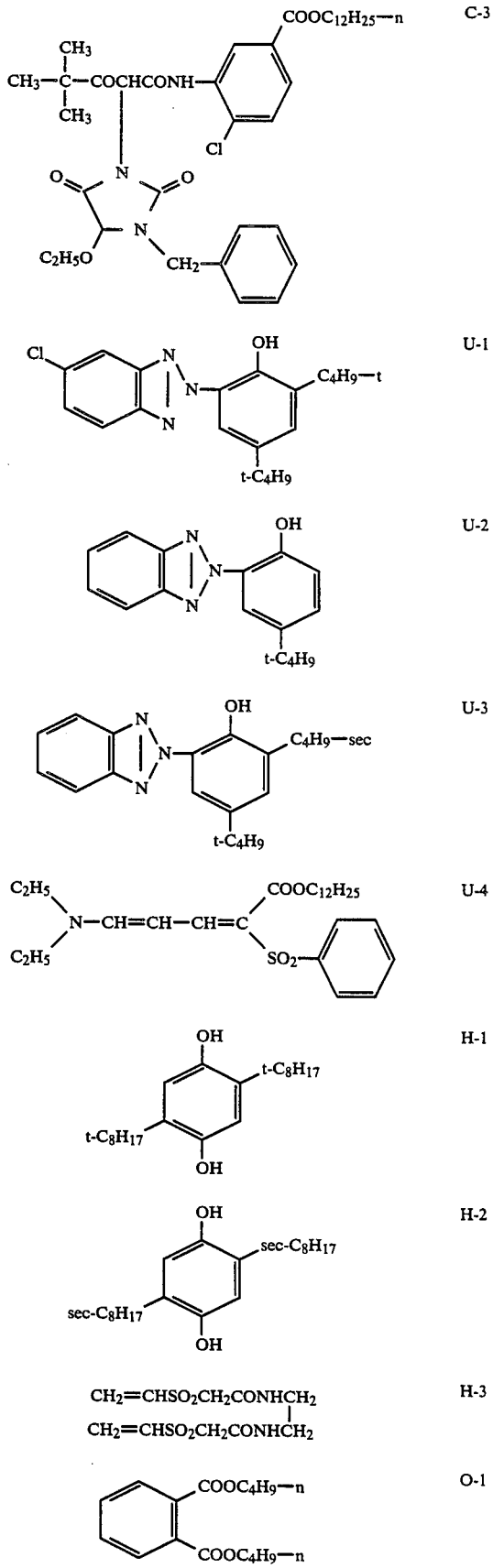

-continued

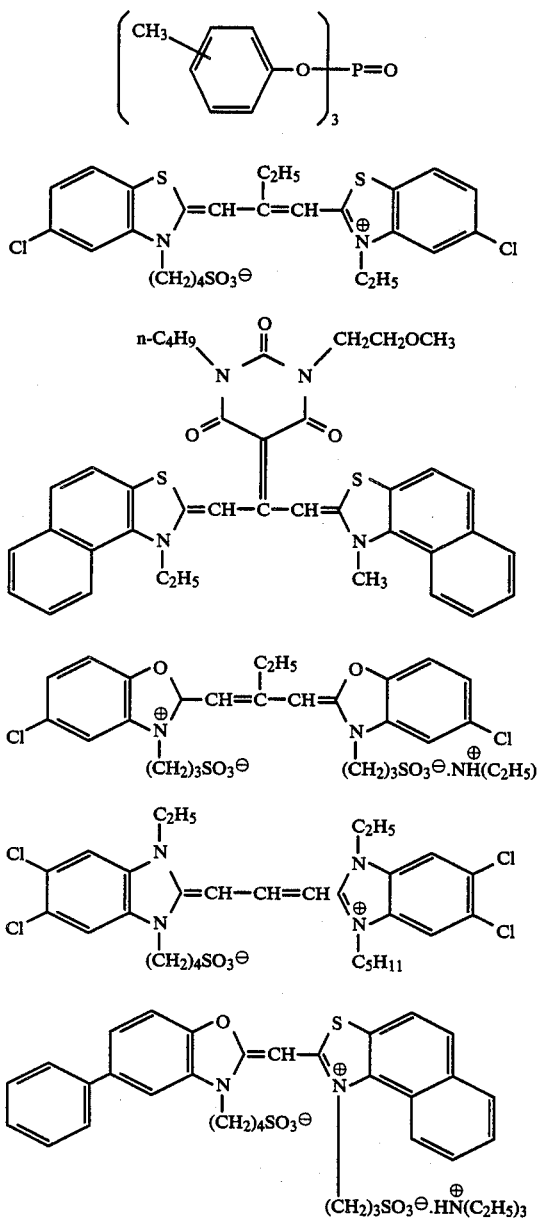

Further, Sample Nos. 302 to 318 were prepared in the same manner as Sample No. 301 except for changing the coupler (C-1) used in the eleventh layer to those shown in Table 6.

The thus prepared films were exposed through a wedge for a sensitometry to white light from a 4,800° K. light source. Then, the color images were obtained by reversal processing. The optical density of the yellow images among color images was measured through a blue filter. The results are shown in Table 7.

TABLE 6

| Sample No. | Yellow Coupler |
| --- | --- |
| 301 (Invention) | Coupler 1 |
| 302 (Invention) | Coupler 2 |
| 303 (Invention) | Coupler 4 |
| 304 (Invention) | Coupler 6 |
| 305 (Invention) | Coupler 7 |
| 306 (Invention) | Coupler 8 |
| 307 (Invention) | Coupler 9 |

TABLE 6-continued

| Sample No. | Yellow Coupler |
| --- | --- |
| 308 (Invention) | Coupler 10 |
| 309 (Invention) | Coupler 12 |
| 310 (Invention) | Coupler 13 |
| 311 (Invention) | Coupler 14 |
| 312 (Invention) | Coupler 16 |
| 313 (Invention) | Coupler 17 |
| 314 (Invention) | Coupler 18 |
| 315 (Comparison) | Comparative Coupler (B) |
| 316 (Comparison) | Comparative Coupler (C) |
| 317 (Comparison) | Comparative Coupler (E) |
| 318 (Comparison) | Comparative Coupler (F) |

Reversal Processing Steps:

| Step | Time (min) | Temperature |
| --- | --- | --- |
| First Development | 6 | 38° C. |
| Washing with Water | 2 | " |
| Reversal | 2 | " |
| Color Development | 6 | " |
| Adjustment | 2 | " |
| Bleaching | 6 | " |
| Fixing | 4 | " |
| Washing with Water | 4 | " |
| Stabilization | 1 | Room Temperature |
| Drying | | |

The composition of the processing solutions was as follows.

First Developing Solution:

| Water | 700 ml |
| --- | --- |
| Nitrilo-N,N,N—trimethylenephosphoric Acid-5 Sodium Salt | 2 g |
| Sodium Sulfite | 20 g |
| Hydroquinone Monosulfonate | 30 g |
| Sodium Carbonate (monohydrate) | 30 g |
| 1-Phenyl-4-methyl-4-hydroxymethyl-3-pyrazolydone | 2 g |
| Potassium Bromide | 2.5 g |
| Potassium Thiocyanate | 1.2 g |
| Potassium Iodide (0.1% solution) | 2 ml |
| Water to make | 1,000 ml |

Reversal Solution:

| Water | 700 ml |
| --- | --- |
| Nitrilo-N,N,N—trimethylenephosphoric Acid-5 Sodium Salt | 3 g |
| Stannous Chloride (dihydrate) | 1 g |
| p-Aminophenol | 0.1 g |
| Sodium Hydroxide | 8 g |
| Glacial Acetic Acid | 15 ml |
| Water to make | 1,000 ml |

Color Developing Solution:

| Water | 700 ml |
| --- | --- |
| Nitrilo-N,N,N—trimethylenephosphoric Acid-5 Sodium Salt | 3 g |
| Sodium Sulfite | 7 g |
| Sodium Phosphate (12 hydrate) | 36 g |
| Potassium Bromide | 1 g |
| Potassium Iodide (0.1% solution) | 90 ml |
| Sodium Hydroxide | 3 g |
| Citrazinic Acid | 1.5 g |
| N—Ethyl-N—($\beta$-methanesulfonamidoethyl)-3-methyl-4-aminoaniline Sulfate | 11 g |
| 3,6-Dithiaoctane-1,8-diol | 1 g |

-continued

| | |
|---|---|
| Water to make | 1,000 ml |

Adjusting Solution:

| | |
|---|---|
| Water | 700 ml |
| Sodium Sulfite | 12 g |
| Sodium Ethylenediaminetetraacetate (dihydrate) | 8 g |
| Thioglycerin | 0.4 ml |
| Glacial Acetic Acid | 3 ml |
| Water to make | 1,000 ml |

Bleaching Solution:

| | |
|---|---|
| Water | 800 g |
| Sodium Ethylenediaminetetraacetate (dihydrate) | 2 g |
| (Ethylenediaminetetraacetate)iron(III) Ammonium (dihydrate) | 120 g |
| Potassium Bromide | 100 g |
| Water to make | 1,000 ml |

Fixing Solution:

| | |
|---|---|
| Water | 800 ml |
| Sodium Thiosulfate | 80.0 g |
| Sodium Sulfite | 5.0 g |
| Sodium Bisulfite | 5.0 g |
| Water to make | 1,000 ml |

Stabilizing Solution:

| | |
|---|---|
| Water | 800 ml |
| Formaldehyde (37 wt %) | 5.0 ml |
| Fuji Driwel (a trade name of a surface active agent manufactured by Fuji Photo Film Co., Ltd.) | 5.0 ml |
| Water to make | 1,000 ml |

TABLE 7

| Sample No. | Minimum Density | Maximum Density |
|---|---|---|
| 301 (Invention) | 0.08 | 3.25 |
| 302 (Invention) | 0.08 | 3.24 |
| 303 (Invention) | 0.08 | 3.01 |
| 304 (Invention) | 0.07 | 3.03 |
| 305 (Invention) | 0.08 | 3.00 |
| 306 (Invention) | 0.08 | 3.06 |
| 307 (Invention) | 0.07 | 3.01 |
| 308 (Invention) | 0.08 | 3.10 |
| 309 (Invention) | 0.08 | 3.12 |
| 310 (Invention) | 0.08 | 3.12 |
| 311 (Invention) | 0.07 | 3.07 |
| 312 (Invention) | 0.07 | 3.48 |
| 313 (Invention) | 0.07 | 3.45 |
| 314 (Invention) | 0.08 | 3.42 |
| 315 (Comparison) | 0.08 | 2.91 |
| 316 (Comparison) | 0.08 | 2.86 |
| 317 (Comparison) | 0.08 | 2.52 |
| 318 (Comparison) | 0.08 | 2.81 |

It is apparent from the results in Table 7 that the couplers of the present invention exhibit high color density without any change of fog. Therefore, it is possible to reduce the amount of couplers and/or emulsion employed.

The silver halide color photographic material prepared by using the novel yellow couplers of the present invention has the following advantageous effects.

1. Even though a photographic element is developed with a color developing solution which does not contain benzyl alcohol, the color density and gamma of the color images thus obtained are hardly reduced, since the yellow couplers of the present invention have sufficient coupling activity.

2. The yellow couplers of the present invention are not affected by a change in pH of the color developing solution and unevenness of the density of color images can be reduced.

3. The storage stability such as light fastness, heat resistance and moisture resistance of the thus obtained color images is excellent.

4. The yellow couplers of the present invention have high solubility in organic solvents having a high boiling point and good dispersibility and stability in a silver halide color photographic emulsion.

5. The yellow couplers of the present invention have sufficient coupling activity even if the amount of organic solvents having a boiling point is reduced. Therefore, the film thickness of the light-sensitive materials can be reduced.

6. A photographic light-sensitive material prepared by using the yellow couplers of the present invention can be processed at a high temperature and at a high rate of speed.

While the invention has been described in detail and with reference to specific embodiments thereof, it will be apparent to one skilled in the art that various changes and modifications can be made therein without departing from the spirit and socpe thereof.

What is claimed is:

1. A silver halide color photographic material comprising a support having coated thereon at least one light-sensitive silver halide emulsion layer containing a yellow coupler represented by formula (I):

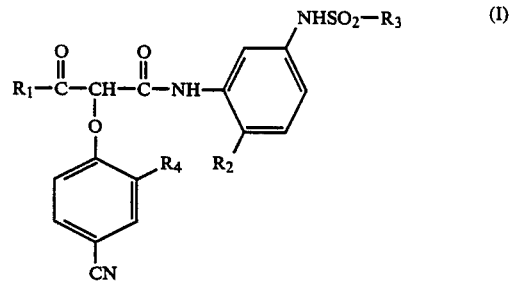

wherein $R_1$ represents a substituted or unsubstituted tertiary alkyl or aryl group; $R_2$ represents a chlorine atom or an alkoxy group; $R_3$ represents a substituted or unsubstituted alkyl or aryl group; $R_4$ represents a chlorine atom when $R_1$ represents a tertiary alkyl group or represents a hydrogen atom or a chlorine atom when $R_1$ represents an aryl group.

2. The silver halide color photographic material as claimed in claim 1, wherein said yellow coupler is represented by formula (II):

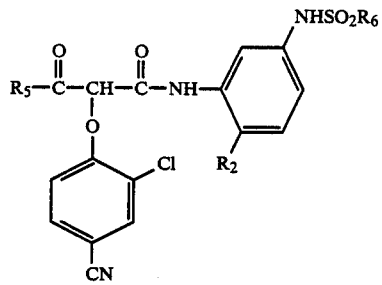

wherein $R_5$ represents a substituted or unsubstituted tertiary alkyl group having from 4 to 8 carbon atoms: $R_6$ represents an unsubstituted alkyl group or an alkyl group substituted by an alkoxy group having from 6 to 20 carbon atoms, or a group represented by formula (III), (IV) or (V):

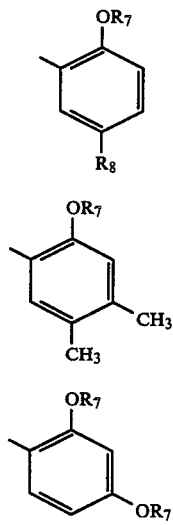

wherein $R_7$ represents an unsubstituted alkyl group or an alkyl group substituted by an alkoxy group having from 1 to 12 carbon atoms, $R_8$ represents a substituted alkyl group having from 1 to 8 carbon atoms; and $R_2$ has the same meaning as that in formula (I).

3. The silver halide color photographic material as claimed in claim 1, wherein the yellow coupler is represented by formula (VI):

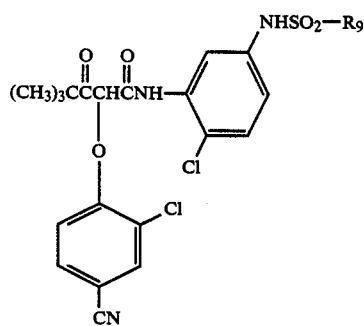

wherein $R_9$ is an unsubstituted alkyl group having from 6 to 16 carbon atoms.

4. The silver halide color photographic material as claimed in claim 1, wherein said coupler is employed in an amount of $2\times10^{-3}$ mol to $5\times10^{-1}$ mol per mol of silver in the emulsion layer.

5. The silver halide color photographic material as claimed in claim 4, wherein said coupler is employed in an amount of $1\times10^{-2}$ mol to $5\times10^{-1}$ mol per mol of silver in the emulsion layer.

6. A process for forming yellow images comprising developing an imagewise exposed silver halide color photographic material comprising a support having coated thereon at least one light-sensitive silver halide emulsion layer containing a yellow coupler represented by formula (I):

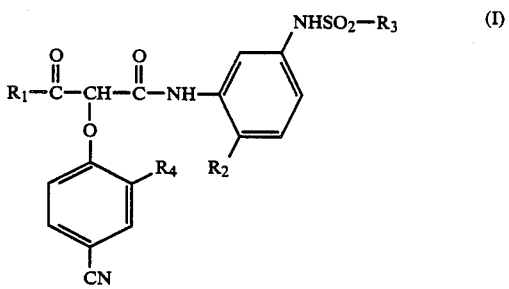

wherein $R_1$ represents a substituted or unsubstituted tertiary alkyl or aryl group; $R_2$ represents a chlorine atom or an alkoxy group; $R_3$ represents a substituted or unsubstituted alkyl or aryl group; $R_4$ represents a chlorine atom when $R_1$ represents a tertiary alkyl group or represents a hydrogen atom or a chlorine atom when $R_1$ represents an aryl group, wherein said material is developed in the absence of benzyl alcohol.

7. The process for forming yellow images as claimed in claim 6, wherein said yellow coupler is represented by formula (II):

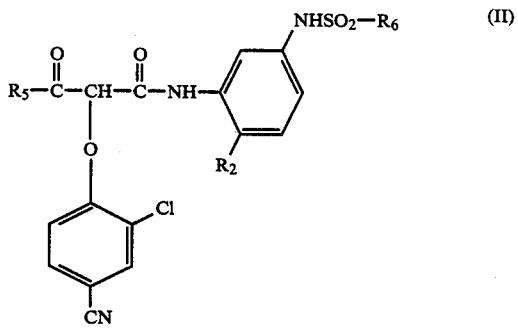

wherein $R_5$ represents a substituted or unsubstituted tertiary alkyl group; $R_6$ represents an unsubstituted alkyl group or an alkyl group substituted by an alkoxy group having from 6 to 20 carbon atoms or a group represented by formula (III), (IV) or (V):

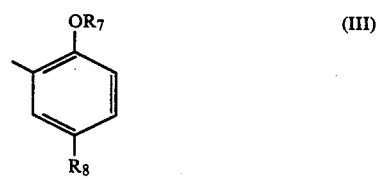

-continued
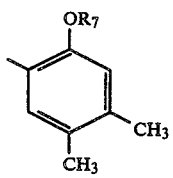
(IV)
-continued
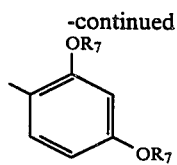
(V)
wherein $R_7$ represents an unsubstituted alkyl group or an alkyl group substituted by an alkoxy group having from 1 to 12 carbon atoms and $R_8$ represents a substituted alkyl group having from 1 to 8 carbon atoms; and $R_2$ has the same meaning as that in formula (I).
* * * * *